(12) United States Patent
McNair et al.

(10) Patent No.: US 12,334,220 B1
(45) Date of Patent: *Jun. 17, 2025

(54) CLINICAL DECISION SUPPORT SYSTEM USING PHENOTYPIC FEATURES

(71) Applicant: CERNER INNOVATION, INC., Kansas City, KS (US)

(72) Inventors: Douglas S. McNair, Seattle, WA (US); John Christopher Murrish, Overland Park, KS (US); Kanakasabha Kailasam, Olathe, KS (US)

(73) Assignee: CERNER INNOVATION, INC., Kansas City, MO (US)

( * ) Notice: Subject to any disclaimer, the term of this patent is extended or adjusted under 35 U.S.C. 154(b) by 93 days.

This patent is subject to a terminal disclaimer.

(21) Appl. No.: 17/531,337

(22) Filed: Nov. 19, 2021

Related U.S. Application Data

(63) Continuation of application No. 15/291,792, filed on Oct. 12, 2016, now Pat. No. 11,183,302.

(60) Provisional application No. 62/240,515, filed on Oct. 12, 2015.

(51) Int. Cl.
*G16H 50/20* (2018.01)
*G16H 10/60* (2018.01)
*G16H 50/70* (2018.01)

(52) U.S. Cl.
CPC ............ *G16H 50/20* (2018.01); *G16H 10/60* (2018.01); *G16H 50/70* (2018.01)

(58) Field of Classification Search
CPC .................................................. G16H 50/20
See application file for complete search history.

(56) References Cited

U.S. PATENT DOCUMENTS

| | | | |
|---|---|---|---|
| 6,047,259 A | 4/2000 | Campbell et al. | |
| 6,266,645 B1 * | 7/2001 | Simpson | G16H 40/20 705/3 |
| 6,278,997 B1 | 8/2001 | Agrawal et al. | |

(Continued)

OTHER PUBLICATIONS

Paul, R., Groza, T., Hunter, J., & Zankl, A. (2012). Decision support methods for finding phenotype—disorder associations in the bone dysplasia domain. PloS one, 7(11), e50614. https://doi.org/10.1371/journal.pone.0050614 (Year: 2012).*

Firth et al., "DECIPHER: Database of Chromosomal Imbalance and Phenotype in Humans Using Ensembl Resources", The American Journal of Human Genetics, vol. 84, No. 4, 2009, pp. 524-533.

(Continued)

*Primary Examiner* — James D. Rutten
(74) *Attorney, Agent, or Firm* — MUGHAL GAUDRY & FRANKLIN PC

(57) ABSTRACT

Systems, methods, and computer-readable storage media are provided for determining and ascribing clinical conditions or diagnoses to patients and provide them to a caregiver, such as attending clinicians or other appropriate health services personnel. In particular, embodiments of the disclosure determine likely phenotypic findings that are salient to the decision-making context for a current human patient, based on anticipative sequence-mining and trajectory-mining. A sequential pattern mining and sequence itemset matching system is provided for determining likely, temporally-relevant concepts that are manifested in the information that is produced during the course of a patient's care. A clinician or caregiver may be provided the sequence itemset matching by generating a list or notice. In addition or alternatively, the results may be stored in an EHR associated with the patient.

20 Claims, 12 Drawing Sheets

(56) References Cited

U.S. PATENT DOCUMENTS

| | | | |
|---|---|---|---|
| 6,486,226 B2 | 11/2002 | Al-Akhdar et al. | |
| 7,177,864 B2* | 2/2007 | Ekhaus | G06F 16/30 |
| | | | 707/E17.058 |
| 7,328,194 B2 | 2/2008 | Dimitriou et al. | |
| 11,183,302 B1 | 11/2021 | Mcnair et al. | |
| 2008/0050749 A1* | 2/2008 | Amann-Zalan | G01N 33/94 |
| | | | 435/7.1 |
| 2009/0327809 A1* | 12/2009 | Joy | G06F 11/3636 |
| | | | 714/E11.026 |
| 2012/0221310 A1 | 8/2012 | Sarrafzadeh et al. | |
| 2013/0080425 A1 | 3/2013 | Kwete | |
| 2013/0238363 A1 | 9/2013 | Ohta et al. | |
| 2014/0292517 A1* | 10/2014 | Hu | G16H 50/20 |
| | | | 340/573.1 |
| 2014/0325587 A1* | 10/2014 | Nilsson | G16B 50/30 |
| | | | 726/1 |
| 2015/0141826 A1 | 5/2015 | Beymer et al. | |
| 2015/0310163 A1 | 10/2015 | Kingsmore et al. | |
| 2017/0011073 A1* | 1/2017 | Deshpande | G06F 16/215 |

OTHER PUBLICATIONS

Guozhu et al., "Sequence Data Mining", Springer Science+Business Media, (Hard Cover Book being mailed on Feb. 28, 2017), 2007, pp. 1-150.

Kadhim et al., "Artificial Neural Networks in Medical Diagnosis", International Journal of Computer Science Issues vol. 8, Issue 2, Mar. 2011, pp. 150-154.

Kenneth et al., "Differential Evolution, A Practical Approach to Global Optimization", Springer-Verlag Berlin Heidelberg, (Hard Cover Book being mailed on Feb. 28, 2017), 2005, pp. 1-539.

Marianna, B. , "Spectral Clustering and Biclustering, Learning Large Graphs and Contingency Tables", John Wiley & D Sons, Ltd, (Hard Cover Book being mailed on Feb. 28, 2017), 2013, pp. 1-268.

Uday, K.C. , "Advances In Differential Evolution", Springer-Verlag Berlin Heidelberg, (Hard Cover Dook being mailed on Feb. 28, 2017), 2010, pp. 1-339.

Wright et al., "The Use of Sequential Pattern Mining to Predict Next Prescribed Medications", Journal of Biomedical Informatics, vol. 53, Feb. 2015, pp. 73-80.

* cited by examiner

EXAMPLE DOWN SYNDROME HPO SEQUENCE TABLE

|  | ITEMS | | | | | |
|---|---|---|---|---|---|---|
| LENGTH | 1 | 2 | 3 | 4 | 5 | 6 |
| 1 | 32 | 0 | 0 | 0 | 0 | 0 |
| 2 | 1 | 181 | 0 | 0 | 0 | 0 |
| 3 | 1 | 86 | 423 | 0 | 0 | 0 |
| 4 | 1 | 79 | 428 | 418 | 0 | 0 |
| 5 | 1 | 52 | 344 | 563 | 184 | 0 |
| 6 | 1 | 16 | 162 | 442 | 286 | 34 |
| 7 | 0 | 1 | 32 | 183 | 231 | 57 |
| 8 | 0 | 0 | 0 | 32 | 93 | 47 |
| 9 | 0 | 0 | 0 | 0 | 15 | 19 |
| 10 | 0 | 0 | 0 | 0 | 0 | 3 |

*FIG. 4A.*

EXAMPLE DOWN SYNDROME SEQUENCE ITEMSETS

| RULE_NUMBER | RULE PRIOR_ITEMS POSTERIOR_ITEMS | SUPP | CONFID | LIFT |
|---|---|---|---|---|
| 1032 | <{HP0008947, HP0000582}> => <{HP0002013}> | 0.250 | 1.0000000 | 2.666667 |
| 1034 | <{,HP0008947, HP0000582}> => <{HP0002013}> | 0.250 | 1.0000000 | 2.666667 |
| 1035 | <{HP0000582}> => <{HP0002013}> | 0.250 | 0.6666667 | 1.777778 |
| 1037 | <{HP0000582}> => <{, HP0002013}> | 0.250 | 0.6666667 | 1.777778 |
| 1039 | <{HP0008947, HP0000582}> => <{, HP0002013}> | 0.250 | 1.0000000 | 2.666667 |
| 1041 | <{, HP0008947, HP0000582}> => <{, HP0002013}> | 0.250 | 1.0000000 | 2.666667 |
| 1042 | <{, HP0000582}> => <{, HP0002013}> | 0.250 | 0.6666667 | 1.777778 |
| 1046 | <{HP0000494}> => <{HP0001488}> | 0.250 | 1.0000000 | 4.000000 |
| 1047 | <{HP0002094}> => <{HP0001488}> | 0.250 | 0.6666667 | 2.666667 |
| 1048 | <{HP0002094}> => <{, HP0001488}> | 0.250 | 0.6666667 | 2.666667 |
| 1049 | <{HP0000494}> => <{, HP0001488}> | 0.250 | 1.0000000 | 4.000000 |
| 1051 | <{HP0000160}> => <{HP0001263}> | 0.375 | 1.0000000 | 2.000000 |
| 1052 | <{HP0000218}> => <{HP0001263}> | 0.250 | 1.0000000 | 2.000000 |
| 1053 | <{HP0000431}> => <{HP0001263}> | 0.500 | 0.8000000 | 1.600000 |
| 1054 | <{HP0000582}> => <{HP0001263}> | 0.250 | 0.6666667 | 1.333333 |
| 1055 | <{HP0002013}> => <{HP0001263}> | 0.250 | 0.6666667 | 1.333333 |
| 1056 | <{HP0002719}> => <{HP0001263}> | 0.375 | 0.7500000 | 1.500000 |
| 1057 | <{HP0002721}> => <{HP0001263}> | 0.375 | 1.0000000 | 2.000000 |
| 1058 | <{HP0002789}> => <{HP0001263}> | 0.250 | 0.6666667 | 1.333333 |
| 1060 | <{HP0008947}> => <{HP0001263}> | 0.375 | 0.7500000 | 1.500000 |
| 1061 | <{HP0010808}> => <{HP0001263}> | 0.250 | 1.0000000 | 2.000000 |
| 1062 | <{HP0011451}> => <{HP0001263}> | 0.250 | 1.0000000 | 2.000000 |
| 1065 | <{HP0011703}, {HP0007930}> => <{HP0001263}> | 0.250 | 1.0000000 | 2.000000 |
| 1066 | <{HP0011703}, {HP0000431}> => <{HP0001263}> | 0.250 | 1.0000000 | 2.000000 |
| 1068 | <{, HP0011703}> => <{HP0001263}> | 0.250 | 0.6666667 | 1.333333 |
| 1069 | <{HP0011623}, {HP0010808}> => <{HP0001263}> | 0.250 | 1.0000000 | 2.000000 |
| 1070 | <{HP0011623}, {HP0007930}> => <{HP0001263}> | 0.250 | 1.0000000 | 2.000000 |
| 1071 | <{HP0011623}, {HP0002721}> => <{HP0001263}> | 0.250 | 1.0000000 | 2.000000 |
| 1072 | <{HP0011623}, {HP0002719}> => <{HP0001263}> | 0.250 | 1.0000000 | 2.000000 |
| 1073 | <{HP0011623}, {HP0000431}> => <{HP0001263}> | 0.250 | 1.0000000 | 2.000000 |
| 1074 | <{HP0011623}, {HP0000160}> => <{HP0001263}> | 0.250 | 1.0000000 | 2.000000 |
| 1076 | <{, HP0011623}> => <{HP0001263}> | 0.250 | 0.6666667 | 1.333333 |
| 1077 | <{HP0011451}, {HP0002721}> => <{HP0001263}> | 0.250 | 1.0000000 | 2.000000 |
| 1078 | <{HP0011451}, {HP0002719}> => <{HP0001263}> | 0.250 | 1.0000000 | 2.000000 |
| 1079 | <{HP0011451}, {HP0000431}> => <{HP0001263}> | 0.250 | 1.0000000 | 2.000000 |
| 1080 | <{HP0011451}, {HP0000218}> => <{HP0001263}> | 0.250 | 1.0000000 | 2.000000 |
| 1081 | <{HP0011451}, {HP0000160}> => <{HP0001263}> | 0.250 | 1.0000000 | 2.000000 |
| 1082 | <{HP0011451}, { }> => <{HP0001263}> | 0.250 | 1.0000000 | 2.000000 |
| 1083 | <{, HP0011451}> => <{HP0001263}> | 0.250 | 1.0000000 | 2.000000 |
| 1084 | <{HP0010808 , HP0000431}> => <{HP0001263}> | 0.250 | 1.0000000 | 2.000000 |
| 1085 | <{HP0000160 , HP0010808}> => <{HP0001263}> | 0.250 | 1.0000000 | 2.000000 |
| 1086 | <{, HP0010808}> => <{HP0001263}> | 0.250 | 1.0000000 | 2.000000 |
| 1087 | <{ }, {HP0010808}> => <{HP0001263}> | 0.250 | 1.0000000 | 2.000000 |
| 1088 | <{, HP0011623}, {HP0010808}> => <{HP0001263}> | 0.250 | 1.0000000 | 2.000000 |
| 1089 | <{HP0011623}, {HP0010808 , HP0000431}> => <{HP0001263}> | 0.250 | 1.0000000 | 2.000000 |
| 1090 | <{ }, {HP0010808 , HP0000431}> => <{HP0001263}> | 0.250 | 1.0000000 | 2.000000 |
| 1091 | <{HP0000160 , HP0010808 , HP0000431}> => <{HP0001263}> | 0.250 | 1.0000000 | 2.000000 |
| 1092 | <{, HP0010808 , HP0000431}> => <{HP0001263}> | 0.250 | 1.0000000 | 2.000000 |

*FIG. 4B*

EXAMPLE DOWN SYNDROME SEQUENCE ITEMSETS SUMMARY

> SUMMARY (R3)
SET OF 3976 SEQUENCERULES WITH

RULE SIZE DISTRIBUTION (1HS + RHS)
SIZES
  2    3    4    5
376  1312 1624  667

RULE LENGTH DISTRIBUTION (1HS + RHS)
LENGTHS
 2    3    4    5    6   7
84   623 1427 1267 499  76

SUMMARY OF QUALITY MEASURES:

| | SUPPORT | CONFIDENCE | LIFT |
|---|---|---|---|
| MIN. | : 0.2500 | MIN. : 0.6667 | MIN. : 0.6667 |
| $1^{ST}$ QU. | : 0.2500 | $1^{ST}$ QU. : 1.0000 | $1^{ST}$ QU. : 1.0000 |
| MEDIAN | : 0.2500 | MEDIAN : 1.0000 | MEDIAN : 2.0000 |
| MEAN: | : 0.2583 | MEAN : 0.9671 | MEAN : 1.7835 |
| $3^{RD}$ QU. | : 0.2500 | $3^{RD}$ QU : 1.0000 | $3^{RD}$ QU. : 2.0000 |
| MAX. | : 1.0000 | MAX. : 1.0000 | MAX. : 4.0000 |

MINING INFO:

| DATA | NTRANSACTIONS | NXEQUENCES | SUPPORT | CONFIDENCE |
|---|---|---|---|---|
| T | 40 | 8 | 0.2 | 0.66 |

FIG. 4C.

EXAMPLE DOWN SYNDROME (PATIENTS 1-5)

| TIME | SEQUENCEID | EVENTID | SIZE | TRANSACTION_BASKET | | | |
|---|---|---|---|---|---|---|---|
| 0 | 1 | 1 | 5 | HP0000582 | HP0008947 | HP0011623 | HP0030148 | HP0011703 |
| 2 | 1 | 2 | 2 | HP0002247 | HP0002013 | | | |
| 5 | 1 | 3 | 3 | HP0003467 | HP0011451 | HP0007930 | | |
| 7 | 1 | 4 | 1 | HP0002721 | | | | |
| 15 | 1 | 5 | 2 | HP0000218 | HP0002719 | | | |
| 17 | 1 | 6 | 4 | HP0000431 | HP0000160 | HP0010808 | HP0006191 | |
| 18 | 1 | 7 | 1 | HP0001263 | | | | |
| 22 | 1 | 8 | 2 | HP0000821 | HP0002488 | | | |
| 0 | 2 | 1 | 7 | HP0000494 | HP0000369 | HP0001643 | HP0000961 | HP0001631 | HP0002094 |
| 12 | 2 | 2 | 2 | HP0030148 | HP0007930 | HP0001488 | | |
| 14 | 2 | 3 | 2 | HP0000316 | HP0008848 | | | |
| 15 | 2 | 4 | 1 | HP0008855 | | | | |
| 16 | 2 | 5 | 1 | HP0002342 | | | | |
| 0 | 3 | 1 | 4 | HP0005469 | HP0000952 | HP0007930 | HP0000431 | |
| 2 | 3 | 2 | 3 | HP0008947 | HP0011623 | HP0011703 | | |
| 3 | 3 | 3 | 2 | HP0001642 | HP0008855 | | | |
| 5 | 3 | 4 | 3 | HP0000767 | HP0000028 | HP0002342 | | |
| 0 | 4 | 1 | 3 | HP0008947 | HP0002251 | HP0011451 | | |
| 1 | 4 | 2 | 1 | HP0002904 | | | | |
| 3 | 4 | 3 | 2 | HP0002721 | | | | |
| 7 | 4 | 4 | 3 | HP0000218 | HP0000431 | HP0000160 | | |
| 9 | 4 | 5 | 1 | HP0001263 | | | | |
| 0 | 5 | 1 | 2 | HP0000582 | HP0008947 | | | |
| 1 | 5 | 2 | 3 | HP0002013 | HP0011703 | HP0002789 | | |
| 4 | 5 | 3 | 2 | HP0007930 | HP0000431 | | | |
| 12 | 5 | 4 | 2 | HP0006191 | HP0001263 | | | |

*FIG. 4D.*

| HPO ID | DESCRIPTION |
|---|---|
| HP0000028 | CRYPTORCHIDISM |
| HP0000160 | SMALL MOUTH |
| HP0000164 | ABNORMAL DENTITION |
| HP0000218 | ARCHED PALATE |
| HP0000316 | HYPERTELORISM |
| HP0000356 | ABNORMAL EAR PINNA |
| HP0000369 | LOW-SET EARS |
| HP0000431 | FLAT NASAL BRIDGE |
| HP0000470 | SHORT NECK |
| HP0000487 | STRABISMUS |
| HP0000494 | DOWNSLANTING PALPEBRAL FISSURES |
| HP0000582 | UPSLANTING PALPEBRAL FISSURES |
| HP0000726 | DEMENTIA NOS |
| HP0000767 | PECTUS EXCAVATUM |
| HP0000768 | PECTUS CARINATUM |
| HP0000821 | HYPOTHYROIDISM |
| HP0000952 | JAUNDICE |
| HP0000961 | CYANOSIS |
| HP0001263 | DELAYED DEVELOPMENTAL MILESTONES |
| HP0001488 | PTOSIS, BILATERAL |
| HP0001631 | ATRIAL SEPTAL DEFECT |
| HP0001642 | PULMONIC STENOSIS |
| HP0001643 | PATENT DUCTUS ARTERIOSUS |
| HP0001852 | FIRST-SECOND TOE SEPARATION |
| HP0002013 | VOMITING |
| HP0002094 | DYSPNEA |
| HP0002247 | DUODENAL ATRESIA |
| HP0002251 | HIRSCHPRUNG'S DISEASE |
| HP0002342 | MENTAL RETARDATION |
| HP0002488 | ACUTE LEUKEMIA NOS |
| HP0002511 | ALZHIMER'S DISEASE |
| HP0002719 | RECURRENT INFECTIONS |
| HP0002721 | IMMUNODEFICIENCY NOS |
| HP0002789 | TACHYPNEA |
| HP0002870 | OBSTRUCTIVE SLEEP APNEA |
| HP0002904 | HYPERBILIRUBINEMIA OF NEWBORN |
| HP0003467 | ATLANTO-OCCIPITAL INSTABILITY |
| HP0004209 | CLINODACTYLY $5^{TH}$ FINGERTIP |
| HP0004279 | SHORT HANDS |
| HP0005469 | FLAT OCCIPUT |

*FIG. 4E.*

SEQUENCE ITEMSET MINING

| a | |
|---|---|
| SID | Itemset |
| 1 | 1 |
| 2 | 1,4 |
| 3 | 1 |
| 4 | |

| b | |
|---|---|
| SID | Itemset |
| 1 | 1 |
| 2 | 3,4 |
| 3 | 2 |
| 4 | 1 |

| c | |
|---|---|
| SID | Itemset |
| 1 | |
| 2 | 2 |
| 3 | 2 |
| 4 | |

| d | |
|---|---|
| SID | Itemset |
| 1 | |
| 2 | |
| 3 | 1 |
| 4 | |

| e | |
|---|---|
| SID | Itemset |
| 1 | 5 |
| 2 | 4 |
| 3 | 4 |
| 4 | |

| f | |
|---|---|
| SID | Itemset |
| 1 | 3 |
| 2 | 4 |
| 3 | 3 |
| 4 | 2 |

| g | |
|---|---|
| SID | Itemset |
| 1 | 3,4 |
| 2 | |
| 3 | |
| 4 | 2 |

*FIG. 5.*

```
###########################################################################

#   identify sequences of 'clusters' of phenotypic features

##################################################################### library(Matrix)
library(arules)
library(arulesSequences)

# notes:
# transactions are epoch-scoped bundles of findings or document terms that are observed in temporal proximity to each other
# [epoch is, say, 30-day window in an infant; 2-year window in adolescent; 180-day window in adult acute conditions; 10-year window in adult chronic conditions]
# in some cases transactions are bundles that are observed together simultaneously [parsed in a single document, say, authored at a single point in time]
# some early bundle-member elements are repeated in most subsequent transactions in a sequence, mainly because they are evocative for the author and reader of what the case is or implies
# some bundle-member elements appear only once in a sequence <{a,b},{c},{a,d}>, sometimes because they were corrected surgically and do not recur
# other bundle-member element terms are repeatedly observed/noted, regardless whether newly incident at time of transaction
<each item that is replicated in a sequence of transactions needs to be de-duped, leaving only the earliest occurrence of the item in the transformed sequence> coarse-graining of time domain (generalization of date) allows semantic quasi-simultaneity for bundle-elements that belong to the same epoch but are smeared across time domain
chaos in categorical timeseries arises
#       (a) because phenotypic features often arise in varying order
#       (b) because clinician observers don't notice them as soon as they are present
(c) because the opportunity to observe is conditional/modal based on patient's access (or lack of it) to health services and severity of illness (or not) meriting such access load example Down Syndrome transaction sequences
t <- read_baskets(con="c:/0_cerdsm/IP/genomics_caredecisions_phenotype_seq_mining/omim190685.csv", sep=",", info=c("time","sequenceID","eventID","SIZE"))
summary(t)

# support: float specifying the minimum support of a sequence (default 0.1, range [0,1])
# maxsize: integer specifying the maximum number of items of an element of a sequence (default 10, range > 0)
# maxlen:  integer specifying the maximum number of elements of a sequence (default 10, range > 0) spanning one or more transactions
# mingap:  integer specifying the minimum time difference between consecutive elements of a sequence (no default)
# maxgap:  integer specifying the maximum time difference between consecutive elements of a sequence (no default)
# maxwin:  integer specifying the maximum time difference between any two elements of a sequence (no default)
```

.
.
.

*FIG. 6A.*   CONTINUES IN FIG. 6B

CONTINUES FROM FIG. 6A

.
.
.

```
# init params and ctrl
# note: decreasing support below 0.02 or increasing maxsize, maxlen, and maxgap dramatically increases runtime
params <- list(support=0.02, maxsize=12, maxlen=10, maxwin=24)
ctrl <- list(verbose=TRUE, tidLists=TRUE)

find sequence itemsets with epochs spanning at most 20 transactions and gaps of up to 24 intervening items
# note: each CSPADE processing of typical-size transaction sequences input leaves GB-size cspadexxxguid.out scratch file in TEMP dir
#      [for example, c:\Users\..\AppData\Local\Temp\RtmpgzmRiK\ ] requiring purging after run is complete
t1 <- Sys.time()
s3 <- cspade(t, parameter=params, control=ctrl)
t2 <- Sys.time()
t2 - t1 summary(s3)
s3.df <- as(s3, "data.frame")

table(length=size(s3, "length"),
    items=size(s3, "items"))

use classification
u <- t
transactionInfo(u)$classID <- transactionInfo(u)$sequenceID %% 2 + 1L
s4 <- cspade(u, parameter=list(support=0.4, maxwin=20))
s4.df <- as(s4, "data.frame")

induce rules from sequences
r3 <- ruleInduction(s3, control=list(verbose=TRUE), conf=0.66)
summary(r3)
r3.df <- as(r3, "data.frame")
r3.df[1:1000,]

# note:
# intervening transaction baskets appear in the sequent itemsets as empty curly braces pairs {}
# optionally post-process the itemsets to strip these

```

*FIG. 6B*

CLINICAL DECISION SUPPORT SYSTEM USING PHENOTYPIC FEATURES

CROSS-REFERENCE TO RELATED APPLICATIONS

This application is a continuation of and claims the benefit of U.S. application Ser. No. 15/291,792, titled "Clinical Decision Support System Using Phenotypic Features," filed Oct. 12, 2016; which claim priority to U.S. Provisional Application No. 62/240,515, titled "Identifying Phenotypic Features for Clinical Decision Making," filed Oct. 12, 2015, which is expressly incorporated by reference in its entirety.

BACKGROUND

Prior attempts to produce artificial intelligence-based diagnostic decision support systems have failed for many reasons. In some cases, the presentation of patients is so widely-varied that it is difficult for an artificial intelligence system to adequately represent the diversity of the phenomena that characterize each condition. For these, the sensitivity and specificity are low, as are the positive predictive value (PPV) and negative predictive value (NPV). In other cases, the non-sequential evolution of a clinical condition, with periods of exacerbation and remission, leads to an intermittency of features such that various predicates associated with the condition are frequently absent, such that the resulting predictive model or system experiences an excessive rate of false-negative determinations in persons who do indeed have the condition.

In other cases, the severity or frequency of the condition exhibits a wide range, and a system that is capable of detecting severe or frequent disease is not adequately capable of recognizing less-severe instances of the same disease. In yet other cases, the number of features needed to produce a system with adequate statistical sensitivity and specificity is so large that it is not practical (for reasons of time, expense, or other factors) to expect any clinician or set of clinicians to supply non-null values for all of, or a sufficient number of, the features required in a fashion that adds to their workload or intrudes upon and disrupts their customary workflow patterns. In still other cases, the style and mode of the system's interaction with the clinician users interferes with the credentials-based, fiduciary role that the clinician has with regard to the patient's care; the system may have less information upon which to base its conclusions or advice, yet it nonetheless acts in a way that may contradict determinations that the clinician has already reached, appearing to countermand the authority and responsibility that lodges with the clinician and, perhaps, augmenting the clinician's risk of medical malpractice claims or other exposures.

In other cases, the decision support system's operations were slow or logistically discordant with the conduct of the care services process, such that the advice provided by the system was tardy, delivered too late to be of use for prevention or therapeutic decisions. Ex post corroboration of decisions that have already been made is of very low value, but ex post discorroboration of decisions that cannot be amended, undone, or redone is of negative value and vehemently disliked by attending clinicians and others.

In yet other cases, the decision support system is only suited to one-time application, assisting in resolving a diagnosis at the time of presentation, and is not amenable to repeated, ongoing application in the care of a patient over time, as certain conditions that were active become suspended or inactive or cured while other new conditions supervene and become active or previously-suspended ones become reactivated.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In various aspects, systems, methods, and computer-readable storage media are provided for determining and ascribing clinical conditions or diagnoses to patients and provide them to a caregiver, such as attending clinicians or other appropriate health services personnel. In particular, embodiments of the disclosure determine likely phenotypic findings that are salient to the decision-making context for a current human patient, based on anticipative sequence-mining and trajectory-mining. A sequential pattern mining and sequence itemset matching system is provided for determining likely, temporally-relevant concepts that are manifested in the information that is produced during the course of a patient's care. A clinician or caregiver may be provided the sequence itemset matching by generating a list or notice. In addition or alternatively, the results may be stored in an EHR associated with the patient.

Some aspects of the disclosure includes a system or method for dynamically directing the care process for single and multi-conditions at key points in time to provide decision support using contextually intelligent aware components. For example, the diagnostic evaluation of the patient may be compressed or accelerated by recommending or suggesting that the user consider concepts or findings that are frequently found among other patients' sequence itemsets at comparable stages or temporal positions in their conditions' progression or the care processes' progression. Relevant phenotype findings, laboratory tests including cytogenetics and genome or exome sequencing, medications, and procedures can be presented to a user or tailored to the user, such as a user-specialty, role, venue, clinical condition(s), or other attributes. An embodiment includes one or more software agents or software routines implemented across a distributed cloud-computing platform for facilitating the services. In some embodiments, the agents or routines are autonomous or semi-autonomous, adaptive, and capable of machine-learning. In so doing, embodiments can provide predictive, preventative, screening and monitoring services, in addition to diagnostic and therapeutic services, for patient conditions and events including overlapping, concurrent or compound conditions and multiple comorbid diagnoses.

Additionally, embodiments of the disclosure may enable reliable determination of relevant differential diagnosis and potential problem list items contemporaneously with the provisioning of care services and in a manner that relies on text that is spontaneously generated as a by-product of the documentation of routine care and does not require changes to clinician workflow or labor-intensive and cognitively-demanding "Tell-and-Ask" interactive dialogue with users.

BRIEF DESCRIPTION OF THE DRAWINGS

The present invention is described in detail below with reference to the attached drawing figures, wherein:

FIG. 4A-4E depict example data and analysis associated with an example embodiment applied to patients with down syndrome, in accordance with an embodiment of the disclosure;

FIG. 5 illustratively depicts example results of various vertical algorithms for sequence item mining, that may be used in accordance with an embodiment of the disclosure; and FIGS. 6A-6B illustratively provide an example embodiment of a computer program routines used for the methods described in connection to FIGS. 2 and 3.

DETAILED DESCRIPTION

Figure 1A:
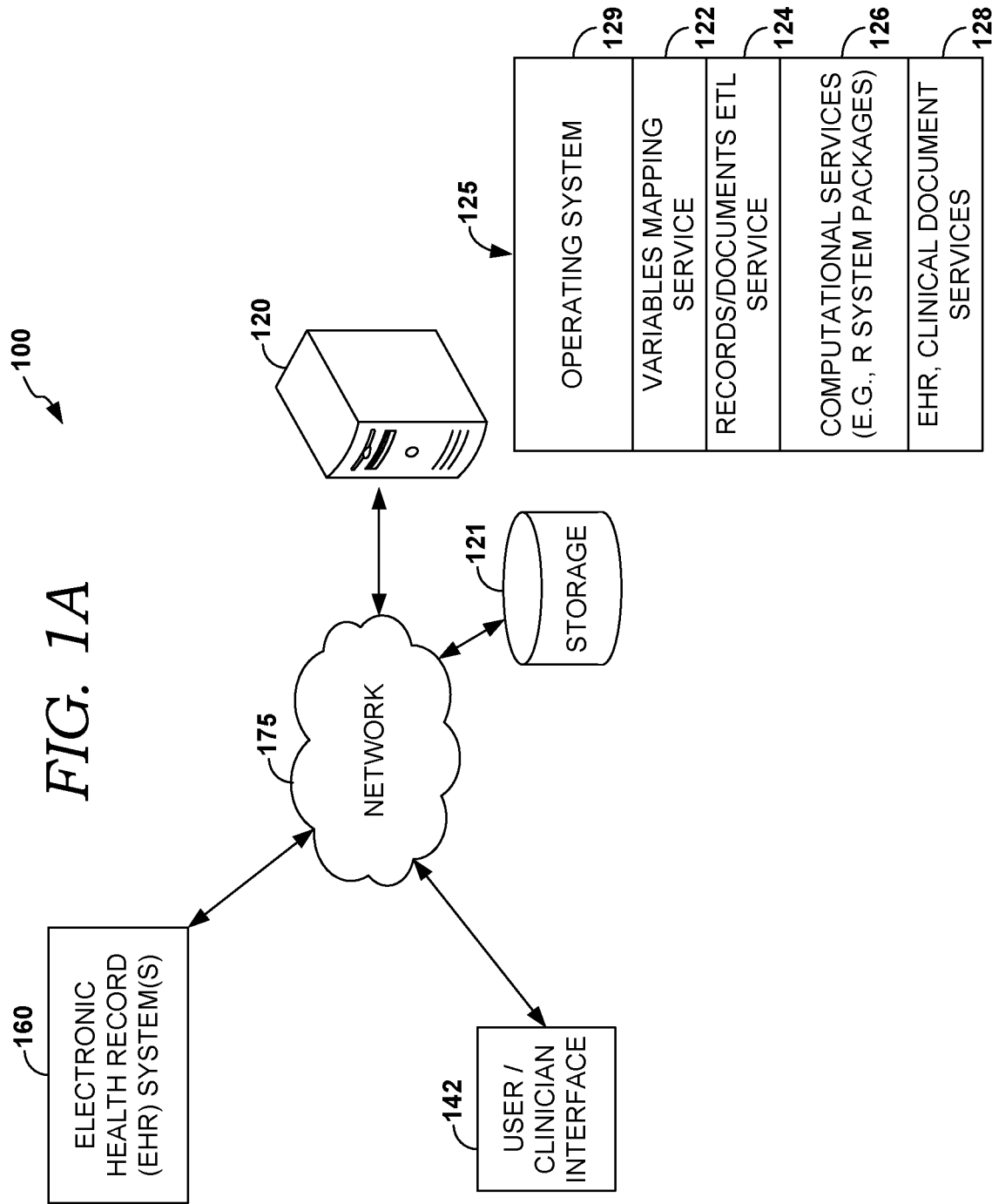
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computing device. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

A patient's medical state continuously changes over time, for instance, one day they may be 'healthy' and the next they may be 'depressed' (health condition 'A', say). It is common for medical states to develop gradually over time and/or be dependent on previous medical states. For example, before developing health condition A, many patients may previously have health conditions B and C (diabetes and kidney failure). If these temporal associations between health condition can be learned, they can be used to highlight patients that have health conditions B and C as being more susceptible to, or in fact having, health condition A. With this knowledge it may be possible to then act to reduce the chance of these susceptible patients developing health condition A, or it may be possible to establish the diagnosis of A earlier than would ordinarily happen. This might be done by performing additional exams or observations or inquiring about conditions B and C and, if present, their symptoms and severity and timing. If preventing the health condition is not possible, susceptible patients may be monitored more frequently to help detect the health condition early, ameliorate its severity and progression, and improve its prognosis.

Sequential patterning mining algorithms find such temporal associations. An example of a sequential pattern rule in the context of retail sales is that 37% of customers buying an milk and beer at a convenience store after 10:00 p.m. return within 15 minutes to buy diapers. Existing work aiming to detect medical sequential patterns has tended to focus on specific health conditions. But other than those efforts described herein, there is currently no existing work on detecting sequential patterns of phenotypic features in genetic disorders, such as provided by embodiments of this disclosure.

As described previously, embodiments of the invention ascribe clinical conditions or diagnoses to patients by determining likely phenotypic findings that are salient to the decision-making context for a patient, based on anticipative sequence-mining and trajectory-mining. The task of diagnosis (e.g., analyzing available data to determine a cause that explains the patient's signs and symptoms) is already challenging. But the diagnostic process is even more challenging in the modern era of healthcare (e.g., deciding which questions to ask and answer; which tests to perform; which alternative differential-diagnostic considerations to entertain; deciding the relative value of the results from the foregoing, compared to the associated risks and financial costs of pursuing answers to various questions, etc.).

The implementation of electronic health records (EHRs) presents a new opportunity to enhance computer-assisted diagnosis, monitoring, prognosis, and longitudinal management in routine practice. EHRs contain many of the data elements critical to establishing a differential diagnosis. Most EHRs' databases contain a patient problem list, including phenotypic findings that relate to conditions other than conventional medical 'diagnoses'. The problem list is described as a key opportunity as a storage modality and workflow moment to offer clinicians diagnostic support. In point of fact, however, a majority of clinicians tends to staunchly refrain from ascribing problem list items in EHRs in a manner that is contemporaneous with their conduct of the care process. Some opine that concurrent attribution of problem list entries is not convenient in their workflow; others assert that they do not wish to create a documentation trail of contemporaneously-entered problem list items that might be utilized by attorney-for-plaintiff in subsequent malpractice claims.

Furthermore, autopsy studies and other research suggest an overall diagnostic error rate of at least 30% in medicine. Most of these are errors-of-omission and failures-to-diagnose (including "failure to diagnose in a timely fashion"), due to cognitive mistakes on the part of the individual practitioner. Premature closure, overconfidence, anchoring and a host of other cognitive mistakes play a role in diagnostic error. While historical efforts in diagnostic support have required entry of patient symptoms and signs and other patient features, the modern prior art systems that automatically retrieve EHR and other contemporary data that allow to begin with either a phenotypic feature, a problem, a presumed diagnosis, a drug, a symptom, or a constellation of any of the above still fail on account of the errors-of-omission and failures-to-diagnose on the part of the human clinicians. The clinician user is frequently unable to adequately interact with the diagnostic decision support systems that depend on human review and input. As such, there are significant improvements current technological processes, which have failed to make reliable assessments or prognoses based on a patient's EHR record.

In that regard, decision support systems, such as HELP at University of Utah and Cerner Corporation's DiscernExpert™ system play a more active and operational role, providing decision-support as a by-product of transaction-processing and inferencing. Such systems do not passively wait for physicians or other health workers specifically to request assistance but instead actively transact provisional orders or emit "alert" messages or interdict transactions that are unsafe or otherwise contraindicated or perform other actions autonomously. The HELP system remains in routine use at University of Utah, and the DiscernExpert™ system is in widespread routine use in more than 2,000 health care facilities world-wide. However, diagnostic decision support is not a prominent aspect of how those systems are utilized, despite the fact that those systems are functionally capable of assisting with diagnoses. The reasons why this is so are substantially the same as the reasons described previously.

In particular, faulty designs for human-computer interaction and inadequate recognition of the logistical and psychological aspects of clinical decision support system use account for a major portion of the failures represented in the foregoing paragraphs. Despite various partial successes in limited or controlled contexts, these approaches continue to have several limitations including: (1) Excessive false-negative rates, often exceeding 40%. (2) Excessive consumption of time for entry and/or review of findings, before the system calculates its classifications or advice. (3) Failure to accommodate different sequences or stages in the conditions' evolution, or different levels of severity that affect the manifestation (or not) of the conditions' characteristic features, or the intermittency of the presence or observability of certain features or phenotypic findings. (4) Failure to identify health conditions other than 'medical' diagnoses. (5) Proneness to misclassification and calibration errors arising from model development in a population of patients that is different from the population that is incident upon the institution where the current patient is receiving care, or development in a health services facility where various factors affecting clinicians' generation of clinical narrative text (factors including staffing levels; workload; the regime of prevalent linguistic expressions in clinical text; the regulations and tort or other normative factors that affect the structure and content of clinical narrative in the jurisdiction; the modes of documenting symptoms and objective findings and clinical assessments and plans; and so forth) are substantially different from those where model development occurred. (6) Requirement to utilize numerous signs and symptoms that require considerable time to enter, to retrieve, or to review and affirm even when they are presented to the user automatically by an online system. (7) Process and workflow intrusions that interfere with ongoing work for the clinician, such that they are disincentivized to permit the intrusions or unrequested demands for her/his time and attention. (8) Failure to incorporate the observations and assessments of multiple clinicians, including clinicians different from the current user, such as most commonly are recorded in unstructured narrative text segments of the EHR. (9) Inability to include longitudinal time-series evidence for or against conditions whose time-trajectory constitutes a significant form of evidence characterizing the conditions, including expressions that are recorded in serial unstructured progress note texts that are date-time stamped at the moment of their deposition in the EHR.

Additional limitations include: (10) a requirement that the user know many or all of the patient's diagnoses or clinical context and be able at the outset to nominate or select these, or to identify sequences in regard to which diagnoses or conditions arose in which order. However, many patients have multiple concurrent/comorbid diagnoses, such that knowing and remembering all of them in a fashion that could be accurately and completely recited into a decision support system is error-prone or cumbersome. Yet other patients have not yet received a diagnosis or diagnoses established at other health institutions are not available or known to the user, such that reciting information that is elsewhere known is (a) not possible for a given individual clinician user at the time that diagnostic decision-making proceeds in the current episode or (b) error-prone insofar as sequences of conditions or diagnoses are not known with adequate certainty.

Still other limitations include: (11) Lack of automatic adaptation to the longitudinally evolving context or physiologic condition of the patient, vis a vis changing and adjusting selections under (10) with the passage of time. (12) Requirement that the system contain the entirety of the lifetime records for the patients, from birth to old age or death, in order to determine similarity of a subsequence to ["textbook case"] idealized sequence itemsets that are historically known from patients who exhibit most or all of the findings that are characteristic or pathognomonic of the condition or constellation of associated conditions. (13) Inability to accurately accommodate matching or sequence itemset similarity determinations in situations involving "composite" constellations of conditions, including co-occurring comorbid conditions or consequences or complications of the primary health condition.

It is therefore valuable that some embodiments of the disclosure ameliorate these limitations and providing objective, quantitative means for automatically discriminating true-positive versus false-positive conditions in near-real-time, to enable diagnostic and therapeutic decision-making to proceed without delay. Further, the methods of embodiments disclosed herein improve the computer's capabilities to search a patient's EHR and derive any worthwhile diagnostic by reducing the time and processing power of the computer.

Accordingly, at a high level, this disclosure describes, among other things, methods and systems, for sequential pattern mining and sequence itemset matching for determining likely, temporally-relevant concepts that are manifested in the information that is produced during the course of a patient's care. In an embodiment, structured and unstructured text data is collected and analyzed from an electronic health record associated with the patient, which may include data accruing during the routine provisioning of care services. In some embodiments, the text may be determined from narratives about the patient provided by a caregiver, and may be transcribed from spoken descriptions of the patient or patient's care. The textual data is analyzed as to topical or concept-oriented expressions it contains that are statistically similar to those associated with various clinical conditions or diagnoses. In particular, in some embodiments, itemsets of patient characteristics, which may include sequences, trajectories, or collections of phenotypic findings, some of which may be temporal, are determined and associated with a degree of likelihood for a clinical conditions or diagnoses. Moreover, some embodiments perform this analysis and itemset identification and/or matching on a very large scale, which may include tens of thousands of data points or dozens of variables. From this analysis, it is determined which condition- or diagnosis-oriented sequence itemsets the information about the patient most closely resembles, if any. In some embodiments, pruning criteria or filtering transformations are applied and the resulting determinations ranked according to likelihood. Further, the resulting determinations may be provided to a responsible clinician and/or may be suggested for consideration as part of sequential constellations of findings associated with differential diagnoses that are pertinent to the management of the current patient.

Embodiments of this disclosure provide methods and a system for facilitating clinical decision support and managing individual patient by entities including physicians, nurses, medical geneticists, caregivers, health care administrators, insurance providers, patients, and other entities. Triggered by deposition of new electronic health record structured data or of new clinical text documents, an embodiment of the invention includes a sequential pattern mining and sequence itemset matching system for determining likely, temporally-relevant concepts that are manifested in the information that is produced during the course of a patient's care. Discovering such latent concepts in both date-time stamped structured information and in date-time stamped ad hoc narrative text-concepts such as have not previously been formally asserted in the findings or problem list or patient's nominal list of active diagnoses, but are nonetheless likely to prevail at the time of the text's authoring or at future times-enables dynamically directing the patient's diagnostic work-up, care processes, management, and prognosis-related decision making and communication; coupling with contextualized decision support information for determining relevant next actions, using information from care plans and pathways, in some cases; and discovering and incorporating new ontologies and composite sequence patterns of ontology terms into decision support services.

Some of the decision support services provided by embodiments of the disclosure, which are further described below, include providing temporal- or sequence-relevant information about patients, including conditions' salient phenotypic findings; recommending certain items of patient information that might be observable or ascertainable from historical information or from interviewing but that has not yet been the subject of examination or history-taking. Such information may include phenotypic items needed to establish further diagnoses, recommendations, or decision support; dynamically generating assessments for obtaining additional patient information based on the mined sequence contexts of other [historical] patients whose transaction sequence itemsets are the most strongly resembling or matched to that of the present patient; data-mining and information discovery services including discovering new knowledge, such as new clinical variables and sequences that are associated with clinical conditions or events and their progression or outcome; identifying or evaluating treatments or sequences of patient care actions and behaviors, and providing recommendations based on this information; intelligent, adaptive decision support services including identifying critical junctures in patient care processes, such as points in time that warrant close attention by caregivers; and other decision support services.

Referring now to the drawings in general, and initially to FIG. 1A in particular, an aspect of an operating environment 100 is provided suitable for practicing an embodiment of our invention. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, example operating environment 100 provides an aspect of a computerized system for compiling and/or running aspects of the invention including collecting and analyzing unstructured text data from electronic health record(s) to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or a plurality of EHR systems such as hospital EHR systems, health information exchange EHR systems, clinical genetics/genomics systems, ambulatory clinic EHR systems, psychiatry/neurology EHR systems, and may be implemented in computer system 120. Similarly, EHR system 160 may perform functions for two or more of the EHR systems (not shown).

Figure 2:
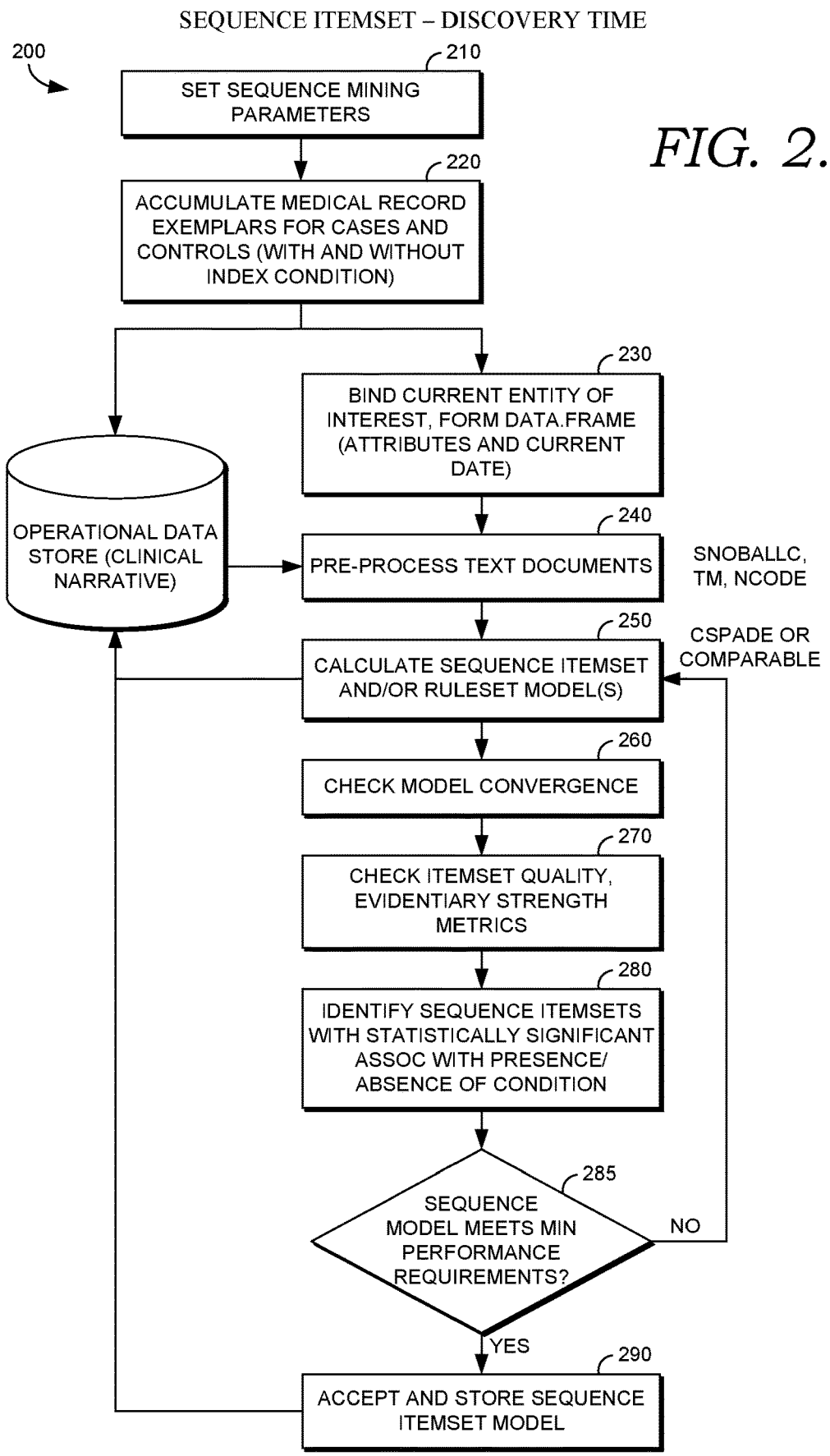
FIG. 2 depicts a flow diagram of a method for discovering reference condition clusters (e.g., sequence itemsets) from EHR data for a population of patients, in accordance with an embodiment of the disclosure.

In some embodiments of the disclosure, sequence itemset mining, such as described in connection to FIG. 2, is performed using data about a population of patients derived from patient EHR information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system 160 include one or more data stores of health records, which may be stored on storage 121, and may further include one or more computers or servers that facilitate the storing and retrieval of the health records. In some embodiments, EHR system 160 may be implemented as a cloud-based platform or may be distributed across multiple physical locations. EHR system 160 may further include record systems, which store real-time or near real-time patient (or user) information, such as wearable, bedside, or in-home patient monitors or sensors, for example.

Example operating environment 100 further includes provider user/clinician interface 142 communicatively coupled through network 175 to an EHR system 160. Although environment 100 depicts an indirect communicative coupling between interface 142 and EHR system 160 through network 175, it is contemplated that an embodiment of interface 142 is communicatively coupled to EHR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A provider clinician application facilitates accessing and receiving information from a user or health care provider about a specific patient or set of patients for which the likely phenotypes or conditions meriting clinician decisions or action are determined, according to the embodiments presented herein. Embodiments of interface 142 also facilitates accessing and receiving information from a user or health care provider about a specific patient or population of patients including patient history; health care resource data; variables measurements, timeseries, and predictions (including plotting or displaying the determined outcome and/or issuing an alert) described herein; or other health-related information, and facilitates the display of results, recommendations, or orders, for example. In an embodiment, interface 142 also facilitates receiving orders for the patient from the clinician/user, based on the results of monitoring and predictions. Interface 142 may also be used for providing diagnostic services or evaluation of the performance of various embodiments.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on interface 142. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 142 and 142. In some embodiments, interface 142 operates in conjunction with software stack 125.

In embodiments, variables mapping service 122 and records/documents ETL service 124 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages including arulesSequences, SnoballC, and tm (text mining), natural language processing services such as Discern nCode™ developed by Cerner Corporation, or similar services. In an embodiment, computation services 126 include the services or routines, which may be embodied as one or more software agents or routines such as the example embodiments of computer program routines illustratively provided in FIGS. 6A-6B. In some embodiments, computation services 126 use EHR or clinical document processing services 128. Some embodiments of stack 125 may further use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Embodiments of storage 121 may include one or more sequence discovery algorithms, such as vertical algorithms, used for sequence itemset mining. Turning briefly to FIG. 5, example results of various vertical algorithms for sequence item mining are illustratively shown in tables a-g. Each table includes a sequence identification (SID) and corresponding itemsets for that SID. Examples of algorithms include, by way of example and not limitation, CSPADE, SPAM, GSP, GlaSP, VMSM, and depth first.

Sequential pattern mining methods find patterns in epoch-ordered temporal sequences. Sequential Pattern Discovery using Equivalence Classes (CSPADE) is a lattice based method and an example of an early sequence discovery algorithm. The CSPADE algorithm is suitable for the medical database due to its ability to find sequences with a high statistical confidence even if the items in the sequence itemsets are quite uncommon, as is the case with most conditions in human medicine. The reason for this is that CSPADE does not require the user to input a minimum value for the support of an item, so rare items (with a low support) can be included into the discovered sequence itemsets or rulesets. In some embodiments these or other similar sequence discovery algorithms are used in method 200, which is described in connection to FIG. 2. These sequential pattern mining methods improve upon the computer's capabilities, in part, by composing effective search schemes and thus minimize the computer's use of memory and computational power.

Figure 1B:
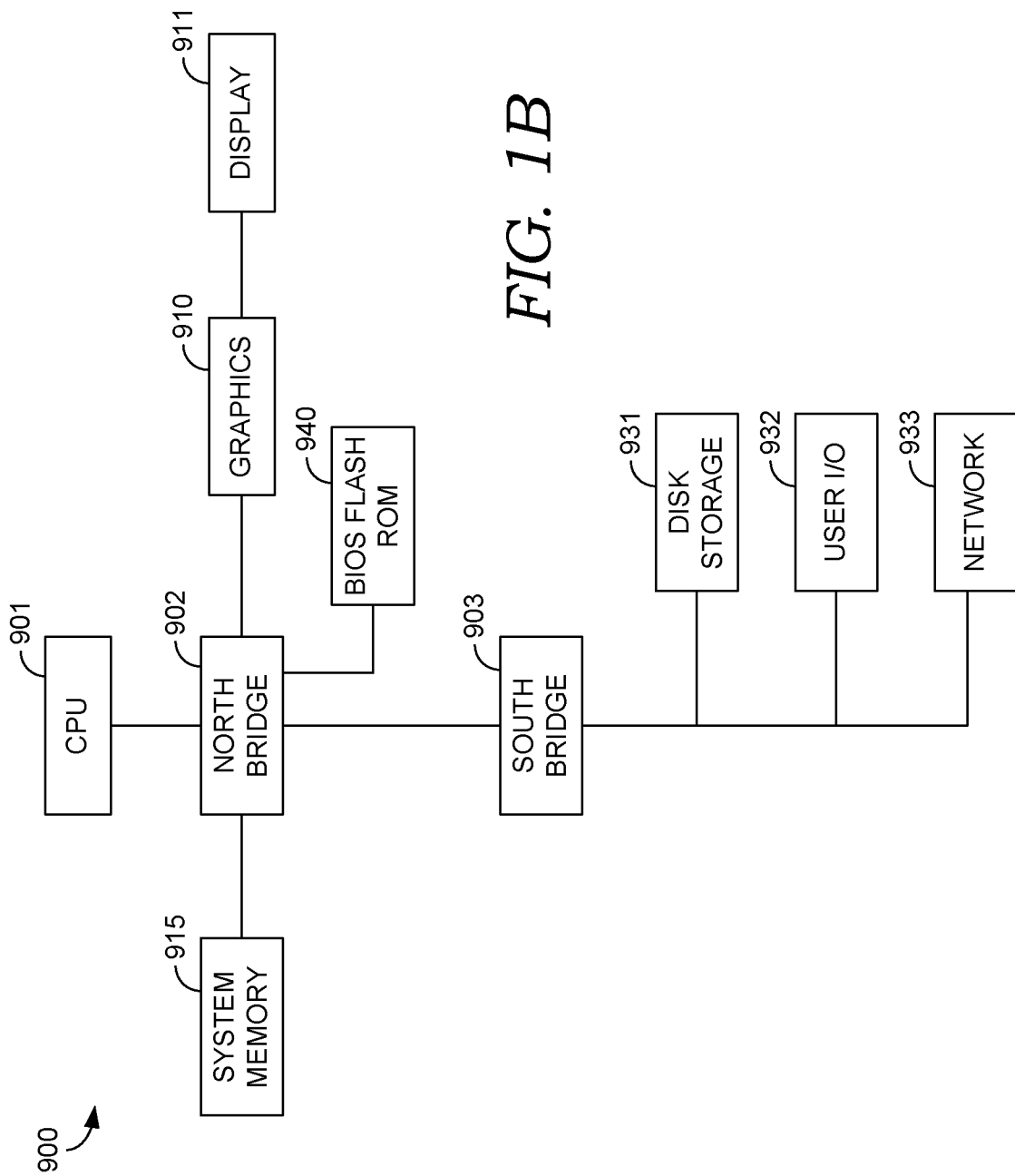

Turning briefly now to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 3:
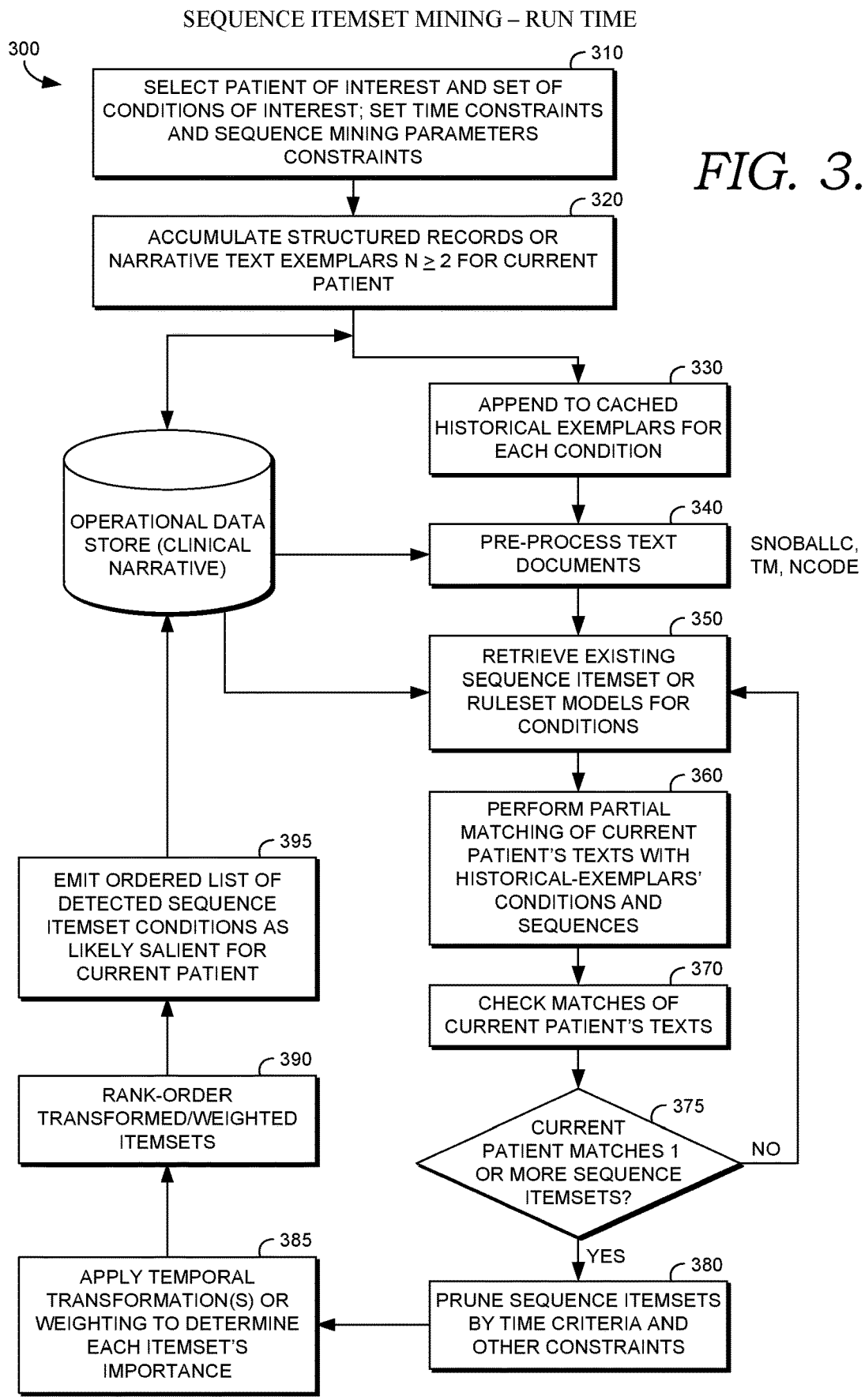
FIG. 3 depicts a flow diagram of a method for determining cluster-membership of a particular patient and their associated EHR data (e.g. matching sequence itemsets), in accordance with an embodiment of the disclosure.

Turning now to FIGS. 2 and 3, an example embodiment of a method 200 for discovering reference condition clusters (e.g., sequence mining of itemsets) from EHR data for a population of patients is provided in FIG. 2, and an example embodiment of a method 300 for determining cluster-membership of a particular patient and their associated EHR data (e.g. matching sequence itemsets) is provided in FIG. 3.

With reference now to FIGS. 2 and 3, generally, compressing the timeline for clinical identification of features comprising inherited syndromes is an important unmet need in health care diagnostics. In that regard, one aim of the example embodiments described in connection to FIGS. 2 and 3 is to support not only the diagnostic use-case (accelerate or reduce the time required to identify and confirm the true diagnosis) but also therapeutic and monitoring and prognostic use-cases, which pertain to anticipative vigilance and the associated preventive actions and/or timely responses to matters that may arise. In this respect, the relevant sequence pattern mining methods of the present invention are similar to those that are used in fault-tree prediction.

Sequential pattern mining is an aspect of data mining and machine learning that is concerned with finding statistically relevant patterns in data where the temporally or spatially arranged values arise as a sequence of transactions. It is usually presumed that the values are discrete, and therefore systems and methods of time series mining are sometimes utilized.

Sequential pattern mining typically deals with a relatively small codeset identifying the various items that can appear in a sequence, but the sequence itself may be typically very long. Examples of an alphabet can be those in the ASCII character set used in natural language text, nucleotide bases 'A', 'G', 'C' and 'T' in DNA sequences, or amino acids for protein sequences. However, in many health-related use-cases the codeset or ontology identifying all of the various items that can occur is quite large, often numbering many tens of thousands or hundreds of thousands or millions of distinct item types.

There are several key computational problems addressed by the present invention. These include building efficient indexes for transaction item sequence information, extracting the frequently occurring patterns, comparing sequences for similarity and frequency (support) and other attributes such as confidence or lift or conviction, and recovering missing sequence members.

Several customary figure-of-merit metrics of association rules' evidentiary strength are support, confidence, lift, and conviction. The support of a sequence itemset X is the prevalence (or frequency within a universe of sequences U) of sequences that contain the sequence itemset X:

$$supp(X) = |\{s|s \in U, X \subseteq s\}| \quad \text{Eq. 1}$$

$$conf(X \rightarrow Y) = \frac{supp(X \cup Y)}{supp(X)} \quad \text{Eq. 2}$$

$$\text{lift}(X \rightarrow Y) = \frac{supp(X \cup Y)}{supp(x) \times supp(Y)} \quad \text{Eq. 3}$$

$$conv(X \rightarrow Y) = \frac{1 - supp(Y)}{1 - conf(X \rightarrow Y)} \quad \text{Eq. 4}$$

In general, sequence mining problems can be classified as 'string mining' (which is typically based on string processing algorithms) and 'itemset mining' (which is typically based on association rule learning).

Despite long and intense effort, to date no broadly effective approach to automatically recommend nosologic entities based on the temporally ordered sequences of conditions or phenotypic concepts that materialize has yet appeared.

With reference to FIG. 2, example method 200 begins at step 210, initializing sequence mining parameters. For example, set sequence mining parameters, including maxwin, maxlen, mingap, and mingap in the CSPADE algorithm, or their corresponding parameters in other sequence mining algorithms, such as shown in the example program routine illustratively depicted in FIGS. 6A and 6B. At step 220, accumulate medical record exemplars for cases and controls (with and without index condition). Embodiments of step 220 may acquire a collection of historical text documents pertaining to, and arising in the course of, the care of an individual patient for analysis, each document bearing meta-data (labeling) ascribing the presence or absence of one or more findings or observational features or phenotypic conditions that prevailed at the time of the document's authoring for the patient who was the subject of the document.

At step 230, bind current entity of interest, such as form data frame (attributes and current date). Embodiments of step 230 bind the record of a target condition predicate or diagnosis entity (from electronic medical records ontology/nomenclature system). At step 240, pre-process the text documents according to means as are known to those practiced in the art of automated natural language processing, including by way of example and not limitation stop-word removal, word-stemming, lowercase transformation, and punctuation/whitespace stripping. Some embodiments of step 240 may apply the SnoballC and nCode computational services 126, described in FIG. 1, such as shown in the example program routine shown in FIGS. 6A and 6B.

At step 250, calculate a sequence itemset model associating encoded terms in the collection of documents with the meta-data labels. Embodiments of step 250 may use the CSPADE algorithm or similar sequence mining algorithms such as those described in connection to FIG. 5.

At step 260, check for model convergence. In particular, embodiments of step 260 may check for convergence of the sequence mining model by examining the iteration-to-iteration objective-function time-series, as a function of iteration index. At step 270, check itemset quality, evidentiary strength metrics. In some embodiments, step 270 comprises determining quality metrics for the resulting sequence itemsets, such as support, confidence, and/or lift. At step 280, identify sequence itemsets with statistically significant association with presence/absence of condition. In some embodiments, identified itemsets may be pruned based on minimum thresholds for one or more metrics determined in step 270. Moreover, in some embodiments, method 200 optionally removes empty intercalated baskets from the pruned sequence itemsets.

At step 285, it is determined whether the sequence model meets performance requirements, which may be determined based on the minimum thresholds for one or more metrics determined in step 270, in an embodiment. If not, then method 200 returns to step 250 to determine sequence itemset and/or ruleset model(s). In other words, if the performance is not acceptable, then recalculate, using perhaps different parameters and/or different text documents. If the sequence model meets performance requirements, then method 200 continues to step 290. At step 290, accept and store the sequence itemset model. Embodiments of step 290 store the sequence pattern mining model and pruned, post-processed sequence itemsets and rulesets that satisfy the criteria that were set. The sequence itemset model may be applied to identify matching sequences in particular patients in order to determine conditions or provide diagnoses, such as further described in FIG. 3.

With reference to FIG. 3, an example is provided of method 300 of applying an existing sequence pattern mining reference model to newly-accruing information for an as-yet-unclassified patient. In particular, the patient may be classified (e.g., as having a condition or diagnoses) based on the application of method 300. Embodiments of method 300 may use a sequence pattern mining reference model determined in method 200, described in FIG. 2.

At step 310, determine a patient of interest and set of conditions of interest; set time constraints and sequence mining parameters constraints. At step 320, accumulate structured records or narrative text exemplars n>2 for current patient. Some embodiments of step 320 comprise retrieving a collection of at least 2 health records or documents pertaining to, and arising in the course of, the care of an individual patient for analysis, for which meta-data (labeling annotations) ascribing the presence or absence of one or more conditions that prevail at the time of the document's authoring for the patient who is the subject of the documents may or may not have been applied.

At step 330, append to cached historical exemplars for each condition. In particular, bind the records of one or more target condition predicates or diagnosis entities of interest (from electronic medical records ontology/nomenclature system). At step 340, pre-process a plurality of the current patient's documents or electronic health information according to means as are known to those practiced in the art of automated natural language processing, including stopword removal, word-stemming, lowercase transformation, and punctuation/whitespace stripping. Some embodiments of step 330 may apply computational services 126 including snoballC, tm, and Discern nCode™.

At step 350, retrieve one or more existing sequence itemset or sequence ruleset models and the identified historical sequence itemsets pertaining to the condition predicates or diagnosis concept entities. At step 360, perform partial matching of current patient's texts with historical-exemplars' conditions and sequences. In an embodiment, step 360 comprises performing K-means or other matching of the current patient's processed information with exemplar sequence itemsets. At step 370, check matches of current patient's texts. If the current patient matches one or more sequence itemsets, at step 375, then method 300 proceeds to step 380. If not, then method 300 proceeds back to step 350. At step 380, prune the matched itemsets according to determined time constraints or mathematical time transformation weighting. At step 385, calculate the rank of members of the resulting pruned matched itemsets. For example, in one embodiment, apply temporal transformation(s) or weighting to determine each itemset's importance.

At step 390 assemble an ordered list of identified significant itemsets and at step 395 provide the list to an appropriate human clinician user. Embodiments of step 395 may provide the ordered list via electronic health record (EHR) software system, and record evidence of having done so in the EHR, for example. If no temporally context-relevant itemset or condition is ascertained, then the patient is deemed not to presently manifest any of the conditions for which reference sequence itemsets have been determined. No notice is emitted or otherwise provided to the human clinician user; however, the system may optionally deposit a date-timestamped record in the EHR as evidence of the then-negative determination, in some embodiments. In some embodiments, an assessment that the current patient conditions may be diagnosed as having an illness or condition is generated and delivered to the appropriate human clinician. For example, the assessment may be provided as an indication or recommendation and may be presented to or otherwise communicated to a clinician or other caregiver associated with the patient.

With reference now to FIGS. 4A, 4B, 4C, 4D, and 4E, an example is described of one embodiment of the invention reduced to practice for determining a personalized sequence itemsets pertaining to evolving features of Down Syndrome. In particular, the example condition of Down Syndrome (Trisomy 21) was utilized as an illustrative example for a reduction to practice. Down Syndrome, the most frequent form of mental retardation caused by a microscopically demonstrable chromosomal aberration, is characterized by well-defined and distinctive phenotypic features and natural history. It is caused by triplicate state (trisomy) of all or a critical portion of chromosome 21. In some instances, there is 'mosaicism' of the body's cells, so that the amount of chromosome 21 that is replicated varies among the cells. In other instances, there is more than one extra copy of portions of chromosome 21 in cells. In yet other instances, there is exactly one extra copy of a complete chromosome 21 in the cells. Many other genetic and genomic abnormalities are statistically associated with Trisomy 21, including mutations in the GATA1 gene and somatic mutations in the JAK2 gene. These various forms of Down Syndrome tend to exhibit different severities, different propensities to develop complications such as acute leukemias, and other aspects.

From a subset of the Down Sydrome cases in Cerner Health Facts® data warehouse and their associated date-time stamped transaction records, a sequence ruleset comprising 16,902 sequential rules was determined by CSPADE, offering a variety of information. The sequence rules contain information about differences in the epochal timing of various Down Syndrome-related phenotypic features' becoming manifested, differences in phenotypic findings' frequency or severity, how age is related to certain phenotypic features and other health conditions that may occur while Down Syndrome's sequelae progress. For example, in the case of persons with Down Syndrome, later life is often affected by recurring infections (due to immunodeficiency), Alzheimer's dementia, and other health conditions that generally are not manifested during childhood or early adulthood.

For some consequences, including ones that are associated with genetic or inherited conditions, the phenotypic antecedents may not lead to or cause the consequence but are linked by the population subgroup with the highest prevalence of the consequent event. These rules carry additional importance or decision-making value as they are non-obvious and may help identify patients at risk of a future health condition by suggesting phenotypic findings or conditions that are prevalent in their population subgroup or are temporally likely to occur in the future in members of the subgroup who do not yet manifest those findings or conditions.

The limitations with applying sequential pattern mining to all patients in electronic health records systems is that most patient sequences are not usually complete. The patient may have received care services elsewhere, such that the records from those other venues are not linked to the electronic health records at the current location. Likewise, the patient may not have assented to permit such linkage even when it is technically available.

When there are discontinuities or gaps in the sequence of transactions in which sequence matches are being sought, it is difficult to distinguish, for example, between real repeat infections or repeat episodes pertaining to the same infection. If sequential pattern mining were applied to sequences of patients that have complete records from birth to death, then the set of rules obtained would be complete. But most patients who are the subject of active care-related decision-making are still alive and only have entries for their life to-date recorded. This may bias the results, as if at age 2 years most people with Down Syndrome manifest 'intellectual disability' and these people are also likely to develop 'Alzheimer's Disease' by age 50 but their subsequences are limited to the patient's present age 4 years then, as they are still included for the support and confidence calculations, the support and confidence of the rule 'mental disability'→'Alzheimer's Disease' in the context of Down Syndrome will be much lower than it should be.

Despite this limitation, the effect may actually help to weight sequential itemsets and rulesets as sequential rules that occur over a shorter time interval are less likely to be affected by only having a partial sequence than sequential rules that occur over many years or decades-long epochs, and these shorter-interval sequential rules are of greater interest to clinicians due to their time-oriented saliency.

Accordingly, in this example reduction to practice, records were randomly selected from a patient health records data warehouse, which is derived from Cerner electronic health record (EHR) from 100% of episodes of care that are incident upon the participating health institutions. The personally-identifiable information was removed in conformance with U.S. HIPAA law and regulations, and the de-identified data were stored in a separate, secure database. For this example, methods 200 and 300 were applied, using the CSPADE algorithm, in an operating environment such as described in FIGS. 1A and 1B., as further described below.

Using word-stemming and transformations such as are supported in open-source software packages SnowballC, and tm, application of the present invention in this instance was able to identify positive cluster-membership with 96% sensitivity and 92% specificity. Encoding of phenotypic features contained in the parsed information was performed using Cerner Discern nCode natural language processing system, utilizing the Human Phenotype Ontology (HPO; http://www.human-phenotype-ontology.org/) codeset to denote the concept terms in the processed records. The Online Mendelian Inheritance in Man® (OMIM; http://omim.org/) codeset was utilized for encoding diagnoses. Without limitation, other codesets, such as SNOMED-CT (http://ihtsdo.org/snomed-ct/) or GENATLAS (http://genatlas.medecine.univ-paris5.fr/imagine/phenotype.php?menu=phenotype), may be used for encoding phenotypic findings or observational features and conditions and for encoding medical diagnoses.

The example reduction to practice was accomplished using a computer running the Linux operating system, the open-source statistical software package R and the R module arulesSequences, SnowballC, tm, and smdc. Stream processing of the accruing documents series was accomplished using Discern DAAKOS and Discern nCode™ software. In this regard, a cloud-based computing configuration is one alternative preferred embodiment of the invention. Alternatively, a stand-alone server or other computing device equipped with suitable connectivity to the device(s) by which the time series are acquired may likewise be utilized in another embodiment.

From data acquired from in-patient hospital subjects and stored in the inventors' organization's data warehouse, a corpus of primary care physician and medical geneticist notes from 200 distinct patients was extracted, 100 each from patients who had a diagnosis of Down Syndrome (Trisomy 21) and from age- and gender-matched patients who did not have this diagnosis.

In this example embodiment, the CSPADE algorithm was adapted for use with Cerner Corporation's Discern nCode™ natural language processing system to process medical narrative text and other structured EHR records, extract HPO phenotypic codes, and identify sequence itemsets and rulesets having a confidence of 0.10 or greater using the cspade function in the arulesSequences R package. The confidence value of 0.10 was chosen for efficiency and to prevent an excessive number of itemsets and rulesets from being determined.

With continuing reference to FIGS. 4A-4E and with reference to the example computer program routines in FIGS. 6A and 6B, for the CSPADE algorithm, the parameter maxwin limits the maximum time difference between datetime stamped transaction baskets in a sequence of one or more itemsets that may span a plurality of transactions or care encounters, regardless whether they are consecutive or nonconsecutive. The parameter maxlen limits the number of transaction baskets in a given sequence. This parameter was not set because there was no theory regarding the maximum number of terms that might occur in a bona fide workup sequence. This is particularly useful insofar as new data may reveal new patterns or sequences that are subtle or longer or more complex than ones that have been previously known or published. Mingap and maxgap are parameters indicating the range of time between consecutive items in a given sequence. Mingap limits the minimum time difference between consecutive transaction baskets in a sequence. Maxgap limits the maximum time difference between consecutive baskets in a sequence.

To increase interpretability, maxgap could be set to 1 so that consecutive episodes in a workup sequence would indicate maneuvers used in consecutive attempts where the subsequent attempt was guided by the antecedent one, rather than maneuvers used in some noncontiguous attempts. But such fastidious serial attention to the findings of other clinicians is an ideal scenario that seldom prevails in routine practice. More commonly, successive clinicians who examine a new patient tend to adopt a skeptical stance with respect to the observations previously made by others, and aim to make and report their own observations independently and without being prejudiced by the observations of others. Additionally, referrals to disparate specialists result in schedules that materialize in no particular order, according to logistical convenience, availability, insurance coverages or restrictions, and the like. In some embodiments, mingap was set to zero to indicate that baskets may be contiguous, even though they are not required to be so.

Prior art and other approaches to solving the problems outlined previously solicit information from the clinician users in a manner that is generic and gives the impression that the system is unaware of the current status of the patient or the recent actions and assertions of the user and her/his colleagues, forcing the user to enter information or respond to questions whose answers are already present in the EHR. This not only wastes valuable time and impairs usability; it also breaches the user's trust in the system and is psychologically discordant with the notion that the system is designed to help the user in a timely way and behave in manner resembling an intelligent, context-aware human assistant. By contrast, some of the embodiments described herein present invention correctly infers similarity to transaction sequences that are associated with specific age- and gender-relevant diagnoses and seeks responses to a small number of timely and quickly- and easily-answered questions that can accelerate the diagnostic process, buttress the documented evidence substantiating the indicated status and automatically driving further specific recommendations as to components of the clinical plan of care, concurrently with the conduct of the care process.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

Embodiment 1. A method for assessing a human patient, including a plurality of unstructured textual records pertaining to observational findings, subjective complaints, clinical assessments, and progress and diagnostic and/or therapeutic plans regarding the patient's care, to determine the likely presence or absence of one or more phenotypic features or conditions or to suggest which additional features or conditions are comparatively more likely than others in light of features and conditions previously observed and recorded and which of these merit consideration by the clinicians who are attending the patient.

Embodiment 2. A means of statistically assessing the patient comprises sequence mining, to establish possible candidate features that are temporally statistically likely to be present or to materialize at a future time in the present patient, given various known features or conditions prevailing in or absent from a corpus of structured records or unstructured textual records resulting from the care processes conducted in a set of prior historical patients and such as have been determined from said corpus. The embodiment including a method of sequential pattern mining, said method comprises the steps of: selecting constraints of elapsed time, number of exams, or other criteria pertaining to the span of observation that is the subject of a diagnostic, clinical management, monitoring, or prognostic process; selecting a constraint of what nomenclature or lexical term codeset or codesets shall be the basis for asserting items as belonging to particular timed transactions or epochal collections of information; selecting the minimum prevalence (or 'support') that shall be deemed sufficiently frequent to merit further consideration for modeling and matching processes; selecting a constraint regarding the maximum gap size in time or number of observations that defines the scope of saliency for the purposes of modeling, matching, or prognostication of future likely features or conditions; selecting a constraint regarding the maximum length or number of terms a given transaction or epochal collection can contain, at most, for purposes of sequence pattern mining; identifying a set of individual items which satisfy the foregoing constraints; producing a set of candidate sequences that satisfy the constraints for the group of historical patients or entities whose records are used to create the sequence itemset models or sequence ruleset models; pruning from the set of candidate sequence itemsets comprised of one or more items such that those sequence itemsets satisfy the selected constraints; counting support for all candidate sequences that pass the pruning step; determining relative salience or relevance of the candidate sequences by applying one or more temporal transformations to filter or weight each itemset or ruleset; ranking or otherwise ordering the resulting filtered or weighted itemsets or rulesets; and rendering the resulting ranked or ordered list to a human user.

Embodiment 3. The method of any of embodiments 1 or 2, the method further comprises a means of establishing cluster membership of the present patient comprises calculating one or more quantitative figures of merit between documents and the terms contained therein that are associated with the present patient and documents of exemplar members of condition-associated term itemset sequences determined by sequence modeling of an historical-patient corpus.

Embodiment 4. The method of any of embodiments 1-3, the method further comprises identification of terms or word-stems that are most strongly associated with particular concepts or topics denoting clinical conditions or diagnoses is performed by a sequence mining algorithm such as CSPADE, SPAM, CM-SPAM, APIN-SPAM, PrefixSpan, CloSpan, GSP, ClaSP, CM-ClaSP, BIDE+, VMSP, MaxSP, VGEN, FEAT, FSGP, GoKrimp or SeqKrimp, TSP, SeqDIM, or a combination or ensemble of sequence mining algorithms such as SPMF.

Embodiment 5. The method of any of embodiments 1-4, the method further comprises identification of the top-N exemplars whose textual content most strongly embodies statistical association with a condition-labeled temporal itemset sequence is determined by CSPADE, TKS, or similar top-N sequence-mining algorithms.

Embodiment 6. The method of any of embodiments 1-5, the method further comprises a selection of the most salient itemset sequences is determined by applying one or more time interval criteria to the sequence itemsets or itemset association rules.

Embodiment 7. The method of any of embodiments 1-6 wherein selection of the most salient itemset sequences is established by applying one or more mathematically determined weights or importance factors to each itemset or association rule according to its time coordinate with respect to the matched terms that have been ascertained for the current records for the present patient.

Embodiment 8. The method of any of embodiments 1-7 wherein members of the resulting itemset subsets to propose or to display to the user are pruned to satisfy saliency criteria for the user's purpose, based on the members' meeting applicable time interval or temporal-relevancy weighting thresholds.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A method for generating one or more sequence itemset models to determine whether a human patient has clinical conditions, the method comprising:
   acquiring data associated with at least one electronic health record for a first set of clinical condition patients and a first set of control patients;
   determining a first codeset for the data associated with at least one electronic health record for the first set of clinical condition patients and the first set of control patients;
   analyzing the first codeset to identify a first statistically significant sequence itemset for a first clinical condition that is supported by the first set of clinical condition patients and is not supported by the first set of control patients, wherein the first statistically significant sequence itemset has a first confidence value of at least 0.10 within a first epoch duration that depends on patient age;

acquiring data associated with at least one electronic health record for a second set of clinical condition patients and a second set of control patients;
determining a second codeset for the data associated with at least one electronic health record for the second set of clinical condition patients and the second set of control patients;
analyzing the second codeset to identify a second statistically significant sequence itemset for a second clinical condition that is supported by the second set of clinical condition patients and is not supported by the second set of control patients, wherein the second statistically significant sequence itemset has a second confidence value of at least 0.10 within a second epoch duration that depends on patient age;
wherein the first epoch duration differs from the second epoch duration; and
generating the one or more sequence itemset models using the first statistically significant sequence itemset and the second statistically significant sequence itemset to analyze an electronic health record of a human patient to provide an output for determining whether the human patient has the first clinical condition or the second clinical condition.

2. The method of claim 1, wherein the one or more sequence itemset models comprise at least one of CSPADE, SPAM, CM-SPAM, APIN-SPAM, PrefixSpan, CloSpan, GSP, ClaSP, CM-ClaSP, BIDE+, VMSP, MaxSP, VGEN, FEAT, FSGP, GoKrimp, SeqKrimp, TSP and SeqDIM.

3. The method of claim 1, wherein the electronic health record of the human patient is associated with a phenotypic condition.

4. The method of claim 1, wherein the first codeset for the first set of clinical condition patients is associated with phenotypic features, and wherein determining the first codeset for the first set of clinical condition patients further comprises encoding the phenotypic features using natural language processing.

5. The method of claim 1, further comprising providing the output to a user device, wherein the output indicates that the human patient has the second clinical condition.

6. The method of claim 1, wherein acquiring the data associated with the at least one electronic health record for the first set of clinical condition patients and the first set of control patients comprises extracting, from an electronic health record system, data associated with a corpus of primary care physician and medical geneticist notes from a plurality of distinct patients.

7. An artificial intelligence-based diagnostic decision support system for assessing a human patient for clinical conditions, the system comprising:
one or more processors; and
computer memory storing computer-usable instructions that, when used by the one or more processors, perform operations comprising:
acquire a first set of fixed data from an electronic health record system having access to a plurality of electronic health records, the first set of fixed data corresponding to first clinical condition patients having a first clinical condition;
acquire a first set of control data from the electronic health record system, the first set of control data corresponding to first control patients;
acquire a second set of fixed data from the electronic health record system, the second set of fixed data corresponding to second clinical condition patients having a second condition;
acquire a second set of control data from the electronic health record system, the second set of control data corresponding to second control patients;
encode terms in the first set of fixed data, the first set of control data, the second set of fixed data, and the second set of control data;
perform a matching analysis to determine which of the encoded terms are in the first set of fixed data, which of the encoded terms are in the first set of control data, which of the encoded terms are in the second set of fixed data, and which of the encoded terms are in the second set of control data;
based on the matching analysis, determine a first statistically significant sequence itemset for the first clinical condition that is supported by the first clinical condition patients and is not supported by the first control patients and a second statistically significant sequence itemset for the second clinical condition that is supported by the second clinical condition patients and is not supported by the second control patients, wherein the first statistically significant sequence itemset has a first confidence value of at least 0.10 within a first epoch duration that depends on patient age and the second statistically significant sequence itemset has a second confidence value of at least 0.10 within a second epoch duration that depends on patient age;
wherein the first epoch duration differs from the second epoch duration; and
determine data within one or more electronic health records of the human patient that matches the first statistically significant sequence itemset for the first clinical condition or the second statistically significant sequence itemset for the second clinical condition.

8. The system of claim 7, wherein the operations further comprise providing an indication to a graphical user interface that the human patient has the second clinical condition.

9. The system of claim 7, wherein the first sequence itemset is determined using a sequential pattern mining method.

10. The system of claim 7, the operations further comprising prior to determining the data within the one or more electronic health records of the human patient that matches the first sequence itemset for the first clinical condition or the second sequence itemset for the second condition, apply natural language processing including whitespace stripping to the data within the one or more electronic health records of the human patient.

11. The system of claim 7, wherein determining the data within the one or more electronic health records of the human patient that matches the first sequence itemset comprises applying pruning criteria and filtering transformations to the data within the one or more electronic health records of the human patient.

12. The system of claim 7, wherein the matching analysis is performed by a sequence mining model comprising at least one of CSPADE, SPAM, CM-SPAM, APIN-SPAM, PrefixSpan, CloSpan, GSP, ClaSP, CM-ClaSP, BIDE+, VMSP, MaxSP, VGEN, FEAT, FSGP, GoKrimp, SeqKrimp, TSP and SeqDIM.

13. The system of claim 12, wherein the sequence mining model generates a sequence identification and a corresponding lexical term associated with the encoded terms.

14. One or more computer-readable storage media storing computer-usable instructions that, when used by one or more computing devices, cause the one or more computing devices to execute operations to provide a diagnostic decision support system that assesses a human patient, the operations comprising:
  acquiring data from an electronic health record system for a first set of clinical condition patients associated with a first clinical condition and a first set of control patients;
  determining a first codeset for the data for the first set of clinical condition patients and for the data for the first set of control patients;
  analyzing the first codeset to identify a first statistically significant sequence itemset for the first clinical condition that is supported by the first set of clinical condition patients and is not supported by the first set of control patients, wherein the first statistically significant sequence itemset has a first confidence value of at least 0.10 within a first epoch duration hat depends on patient age;
  acquiring data from the electronic health record system for a second set of clinical condition patients and a second set of control patients;
  determining a second codeset for the data from the electronic health record system for the second set of clinical condition patients and the second set of control patients;
  analyzing the second codeset to identify a second statistically significant sequence itemset for a second clinical condition that is supported by the second set of clinical condition patients and is not supported by the second set of control patients, wherein the second statistically significant sequence itemset has a second confidence value of at least 0.10 within a second epoch duration that depends on patient age;
  wherein the first epoch duration differs from the second epoch duration; and
  generating output for determining the human patient has the first clinical condition or the second clinical condition by analyzing one or more electronic health records of the human patient, the analyzing based on the first sequence itemset for the first clinical condition that is supported by the first set of clinical condition patients and is not supported by the first set of control patients and the analyzing based on the second sequence itemset for the second clinical condition that is supported by the second set of clinical condition patients and is not supported by the second set of control patients.

15. The media of claim 14, wherein analyzing the one or more electronic health records of the human patient comprises applying a sequence mining model to data associated with the one or more electronic health records, the sequence mining model comprising at least one of CSPADE, SPAM, CM-SPAM, APIN-SPAM, PrefixSpan, CloSpan, GSP, ClaSP, CM-ClaSP, BIDE+, VMSP, MaxSP, VGEN, FEAT, FSGP, GoKrimp and SeqKrimp, TSP, and SeqDIM.

16. The media of claim 14, wherein the operations further comprise defining at least one sequence mining parameter for analyzing the one or more electronic health records of the human patient via the sequence mining model.

17. The media of claim 14, wherein the first codeset includes a Human Phenotype Ontology and the second codeset includes a Human Phenotype Ontology.

18. The media of claim 14, wherein the one or more electronic health records of the human patient are associated with a time-series corresponding to phenotypic features and an age of the human patient.

19. The media of claim 14, wherein the operations further comprise pruning, prior to analyzing the one or more electronic health records of the human patient, the first sequence itemset based on a time constraint.

20. The media of claim 14, wherein the operations further comprise identifying the first sequence itemset based on a statistical relevance with a presence of the first clinical condition.

* * * * *